(12) United States Patent
Bradway et al.

(10) Patent No.: US 10,905,541 B2
(45) Date of Patent: Feb. 2, 2021

(54) BRANCHED FROZEN ELEPHANT TRUNK DEVICE AND METHOD

(71) Applicant: Cook Medical Technologies LLC, Bloomington, IN (US)

(72) Inventors: Ryan C. Bradway, West Lafayette, IN (US); Woong Kim, West Lafayette, IN (US); Jarin A. Kratzberg, Lafayette, IN (US); Kevin D. Wilger, Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 112 days.

(21) Appl. No.: 15/997,096

(22) Filed: Jun. 4, 2018

(65) Prior Publication Data
US 2019/0365525 A1    Dec. 5, 2019

(51) Int. Cl.
*A61F 2/07* (2013.01)
*A61F 2/89* (2013.01)
(Continued)

(52) U.S. Cl.
CPC .............. *A61F 2/07* (2013.01); *A61F 2/89* (2013.01); *A61F 2002/061* (2013.01);
(Continued)

(58) Field of Classification Search
CPC .... A62F 2/07; A62F 2/89; A62F 2/848; A62F 2002/061; A62F 2002/8486
See application file for complete search history.

(56) References Cited

U.S. PATENT DOCUMENTS

| 5,591,226 A | 1/1997 | Trerotola |
| 5,984,955 A | 11/1999 | Wisselink |

(Continued)

FOREIGN PATENT DOCUMENTS

| EP | 1847234 A1 | 10/2007 |
| WO | WO 01/28453 A2 | 4/2001 |

(Continued)

OTHER PUBLICATIONS

JOTEC Product Brochure—E-vita Open Plus Stent Graft System; pp. 1-8 (Year: 2014).*

(Continued)

*Primary Examiner* — Dinah Baria
(74) *Attorney, Agent, or Firm* — Brinks Gilson & Lione (57) ABSTRACT

An endoluminal prosthesis system for being deployed in a patient's aorta near the heart, includes a graft having a main body with a proximal end configured to be deployed near a patient's heart and a distal end configured to be deployed away from the patient's heart. The main body defines a proximal portion of the graft including the proximal end; a distal portion of the graft including the distal end; a middle portion of the graft extending between the proximal portion and the distal portion. A connection branch attached to the middle portion has an inner end attached to the middle portion and an outer end disposed radially outwardly from the inner end. The outer end of the connection branch includes a terminal ring composed of at least two partial rings pivotable relative to each other and including at least one radially outward barb.

11 Claims, 7 Drawing Sheets

(51) Int. Cl.
*A61F 2/06* (2013.01)
*A61F 2/95* (2013.01)

(52) U.S. Cl.
CPC .............. *A61F 2002/9511* (2013.01); *A61F 2220/0075* (2013.01); *A61F 2230/006* (2013.01); *A61F 2250/006* (2013.01)

(56) References Cited

U.S. PATENT DOCUMENTS

| | | | |
|---|---|---|---|
| 6,773,457 | B2 | 8/2004 | Ivancev et al. |
| 8,002,816 | B2 | 8/2011 | Greenberg |
| 8,128,680 | B2 | 3/2012 | Arnault De La Menardiere |
| 8,287,586 | B2* | 10/2012 | Schaeffer .................. A61F 2/07 623/1.15 |
| 8,915,956 | B2 | 12/2014 | Schaeffer et al. |
| 9,011,517 | B2 | 4/2015 | Hartley et al. |
| 9,044,311 | B2 | 6/2015 | Rasmussen et al. |
| 9,649,188 | B2 | 5/2017 | Hartley |
| 9,662,196 | B2 | 5/2017 | Roeder et al. |
| 9,848,977 | B2 | 12/2017 | Rasmussen et al. |
| 9,993,330 | B2 | 6/2018 | Roeder |
| 10,188,502 | B2 | 1/2019 | Rasmussen et al. |
| 2006/0276883 | A1 | 12/2006 | Greenberg |
| 2008/0264102 | A1 | 10/2008 | Berra |
| 2009/0093873 | A1 | 4/2009 | Navia |
| 2012/0158121 | A1* | 6/2012 | Ivancev .................. A61F 2/06 623/1.13 |
| 2013/0166015 | A1 | 6/2013 | Roeder |
| 2017/0273809 | A1* | 9/2017 | Marmur .................. A61F 2/91 |

FOREIGN PATENT DOCUMENTS

| | | |
|---|---|---|
| WO | 2005046526 A1 | 5/2005 |
| WO | WO 2012/095504 A1 | 7/2012 |
| WO | WO 2014/163957 A1 | 10/2014 |
| WO | 2016098113 A1 | 6/2016 |
| WO | WO 2018/032358 A1 | 2/2018 |
| WO | 2018046917 A1 | 3/2018 |
| WO | WO 2018/060716 A1 | 4/2018 |

OTHER PUBLICATIONS

Product Brochure by JOTEC GmbH, Hechingen, Germany, "E-Vita Open Plus Hybrid Stent Graft System," 5 pages, http://www.jotec.com/en/products/thoracic-stent-grafts/e-vita-open-plus.html.
Product Brochure by Vascutek Terumo, Scotland, United Kingdom, "Thoraflex Hybrid Plexus" and "Thoraflex Hybrid Ante-Flo," 7 pages, http://www.vascutek.com/thoraflex-hybrid/.
Partial European Search Report for corresponding EP Application No. 19178289.5, dated Oct. 23, 2019, 13 pages.
Extended European Search Report for corresponding EP Application No. 19178289.5, dated Jan. 23, 2020, 11 pages.
Extended European Search Report for corresponding EP Application No. 19178291.1, dated Oct. 24, 2019, 8 pages.
Extended European Search Report for corresponding EP Application No. 19178293.7, dated Oct. 25, 2019, 9 pages.

* cited by examiner

BRANCHED FROZEN ELEPHANT TRUNK DEVICE AND METHOD

TECHNICAL FIELD

This invention relates to medical devices for implantation within the human or animal body for treatment of endovascular disease. More particularly, the invention relates to a prosthesis for treating an aorta of a patient.

BACKGROUND OF THE INVENTION

Endovascular methods have been proposed for treatment of aneurysms of the aorta, particularly when an aneurysm is adjacent the aorta bifurcation. But when an aneurysm occurs higher up in the aorta, for example, in the region of the descending aorta adjacent the thoracic arch or in the ascending aorta, endovascular techniques for treating these aneurysms are somewhat more difficult because of the arched nature of the thoracic arch, the existence of major arteries in the region, and the proximity to the heart.

Generally, operations to treat aneurysms that include the ascending aorta or the arch have been done by open chest surgery. Such surgery generally involves surgical replacement of a portion of the aorta with a tubular prosthesis. The surgery is a high risk procedure. Two foremost reasons for the risk associated with the procedure are difficulty of accessing the site of treatment and the potential for neural ischemia.

In dealing with aortic arch aneurysms, procedural risk is greatly increased by inclusion of the brachiocephalic vessels and the aorta distal to the arch. The difficulty of the procedure also may be exacerbated by the necessity to reconnect the left common carotid and left subclavian arteries to the tubular prosthesis after replacing a portion of the aorta.

One method for treating aortic arch aneurysms includes the use of what is known as a frozen elephant trunk. In this approach, a prosthesis is implanted within the aortic arch that is sutured to create a plurality of anastomoses between the prosthesis and the adjacent tissue.

In one approach, the patient is placed on cardiopulmonary bypass. The descending and ascending aorta are transected, giving the surgeon access to the aorta. The elephant trunk prosthesis is placed within the aorta, with a distal end 22 of the prosthesis being released in the distal aorta. This portion of the prosthesis is known as the frozen trunk.

The prosthesis and graft thereof are sutured to the distal aorta to create a distal anastomosis at the descending transection site. Following this anastomosis, the graft is sutured to the innominate, left common carotid, and left subclavian artery to create an anastomosis at these branch vessels. Finally, the proximal end of the graft is sutured to the ascending aorta to create another anastomosis.

The above frozen elephant trunk procedure has its drawbacks. In particular, the quantity and difficulty of suturing each anastomosis presents challenges. Each anastomosis can require approximately half an hour of operating time. This results in a prolonged period of time for the patient on cardiopulmonary bypass and consequently an increased morbidity for the patient.

Although surgical techniques have been successfully demonstrated to repair arch aneurysms, such techniques are highly invasive and thus limited in utility, especially in high risk patients.

SUMMARY

According to a first aspect of the invention, an endoluminal prosthesis system for being deployed in a patient's aorta near the heart includes a graft having a main body with a proximal end and a distal end, where the proximal end is an end configured to be deployed near a patient's heart and the distal end is an end configured to be deployed away from the patient's heart, the main body defining a lumen extending from the proximal end to the distal end; a proximal portion of the graft including the proximal end; a distal portion of the graft including the distal end; a middle portion of the graft extending between the proximal portion and the distal portion; at least one connection branch attached to the middle portion, the connection branch having an inner end attached to the middle portion and an outer end disposed radially outwardly from the inner end, and a lumen extending from the inner end to the outer end, where the at least one connection branch provides fluid communication from the lumen of the graft, through the lumen of the connection branch to the outer end; where the outer end of the at least one connection branch is defined by a terminal ring composed of at least two partial rings pivotable relative to each other, each of the at least two partial rings including at least one radially outward barb.

Implementations may include one or more of the following features. The partial rings may be pivotable relative to each other about an axis perpendicular to a longitudinal direction of the lumen of the connection branch. The at least one connection branch may include a seal stent disposed adjacent the outer end, the seal stent being biased radially outward to engage a branch vessel wall.

Further, the connection branches may be stented such that additional stents are disposed inwardly relative to the seal stent.

Each partial ring may be monolithically formed with the at least one barb. The terminal ring may include an even number of partial rings for collapsibility.

According to another aspect of the invention, an endoluminal prosthesis system for being deployed in a patient's aorta near the heart includes a graft having a main body with a proximal end and a distal end, where the proximal end is an end configured to be deployed near a patient's heart and the distal end is an end configured to be deployed away from the patient's heart, the main body defining a lumen extending from the proximal end to the distal end; a proximal portion of the graft including the proximal end; a distal portion of the graft including the distal end; a middle portion of the graft extending between the proximal portion and the distal portion; at least one connection branch attached to the middle portion, the connection branch having an inner end attached to the middle portion and an outer end disposed radially outwardly from the inner end, and a lumen extending from the inner end to the outer end, where the at least one connection branch provides fluid communication from the lumen of the graft, through the lumen of the connection branch to the outer end; a quick connector forming a connection between the main body and the at least one connection branch. Implementations may include one or more of the following features. The connection formed by the quick connector may be releasable. The quick connector may include a first connector part and a second connector part, the first connector part including a plurality of snap fingers with inward projections and the second connector part including a radially inward step delimits an indentation configured to receive the inward projections. The first connector part may be attached to the at least one connection branch and the second connector part may be attached to the main body of the prosthesis.

According to yet another aspect of the invention, an endoluminal prosthesis system for being deployed in a patient's aorta near the heart, the system includes a graft having a main body with a proximal end and a distal end, where the proximal end is an end configured to be deployed near a patient's heart and the distal end is an end configured to be deployed away from the patient's heart, the main body defining a lumen extending from the proximal end to the distal end; a proximal portion of the graft including the proximal end; a distal portion of the graft including the distal end; a middle portion of the graft extending between the proximal portion and the distal portion; at least one connection branch attached to the middle portion via a releasable quick connector, the connection branch having an inner end attached to the middle portion and an outer end disposed radially outwardly from the inner end, and a lumen extending from the inner end to the outer end, where the at least one connection branch provides fluid communication from the lumen of the graft, through the lumen of the connection branch to the outer end; where the outer end of the at least one connection branch is defined by a terminal ring composed of an even number of partial rings pivotable relative to each other, each of the at least two partial rings including at least one radially outward barb.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings. The drawings are provided herewith purely for illustrative purposes and are not intended to limit the scope of the present invention.

BRIEF DESCRIPTION OF THE DRAWINGS

In the drawings,

FIGS. 6A and 6B show a detail of a further embodiment of a prosthesis for an aortic arc;

FIGS. 7A and 7B show the embodiment of FIGS. 6A and 6B at different stages of assembly;

DETAILED DESCRIPTION

Unless defined otherwise, all technical and scientific terms used herein have the same meaning as commonly understood to one of ordinary skill in the art to which this invention pertains.

The term "distal" means a location or direction that is, or a portion of a device that when implanted is further downstream in the direction of or with respect to blood flow. In the case of aortic intervention, distal means a location further away from the heart. The distal end of a device for aortic intervention may also be referred to as an inferior end.

The term "proximal" means a location or direction that is, or a portion of a device that when implanted is further upstream in the direction of or with respect to blood flow. In the case of aortic intervention, proximal means a location closer to the heart. The proximal end may also be referred to a superior end.

The term "fenestration" means an opening provided through a surface of a prosthesis from the interior of the prosthesis to the exterior of the prostheses and may have a variety of geometries, including circular, semi-circular, oval, oblong, as well as other geometries.

The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. In addition, materials that are not inherently biocompatible may be subjected to surface modifications in order to render the materials biocompatible. Examples of surface modifications include graft polymerization of biocompatible polymers on the materials surface, coating of the surface with a cross-linked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible. Fibers suitable for making textile grafts include polyethylene, polypropylene, polyaramids, polyacrylonitrile, nylon, and cellulose, in addition to the polyesters, fluorinated polymers, and polyurethanes as listed above. Furthermore, bioremodelable materials may also be used singly or in combination with the aforementioned polymer materials. The textile may be made of one or more polymers that do not require treatment or modification to be biocompatible. The graft may be constructed from woven multifilament polyester, for example and without limitation, Dacron™, produced by DuPONT. Dacron™ is known to be sufficiently biologically inert, non-biodegradable, and durable to permit safe insertion inside the human body.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "tubular" refers to the general shape of an endoluminal device which allows the module to carry fluid along a distance or fit within a tubular structure such as an artery. Unless indicated otherwise, a tubular structure provides fluid communication from end to end through an internal lumen. Tubular prosthetic devices include single, branched, and bifurcated devices that may have more than two ends and a plurality of connected lumens. Tubular may refer to any shape including, but not limited to, tapered, cylindrical, curvilinear, or any combination thereof. A tubular device may have a cross-sectional shape that is, circular, substantially circular or the like. However, it should be understood that the cross-sectional shape is not limited thereto, and other shapes, such as, for example, hexagonal, pentagonal, octagonal, or the like are contemplated.

The term "endoluminal" refers to or describes objects that can be placed inside a body lumen or inside a body passageway in a human or animal body. A body lumen or body passageway can be an existing passageway or a body lumen created by surgical intervention and encompasses any duct (e.g. natural or iatrogenic) within the human body and can be formed by blood vessels, respiratory ducts, gastrointestinal ducts, and the like. "Endoluminal device" or "endoluminal prosthesis" thus describes devices that can be placed inside one of these body passageways or body lumens.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

"Longitudinally" refers to a direction, position or length substantially parallel with a longitudinal axis of a reference, for example of a tubular structure or tubular portion, generally along the greatest dimension of the structure or of the portion.

"Circumferentially" refers to a direction, position, or length that encircles a longitudinal axis of reference by an angular distance measured in degrees. The term "circumferential" is not restricted to a full 360° circumferential turn or to a constant radius.

The terms "patient," "subject," and "recipient" as used in this application refer to any animal, especially a human.

Figure 1:
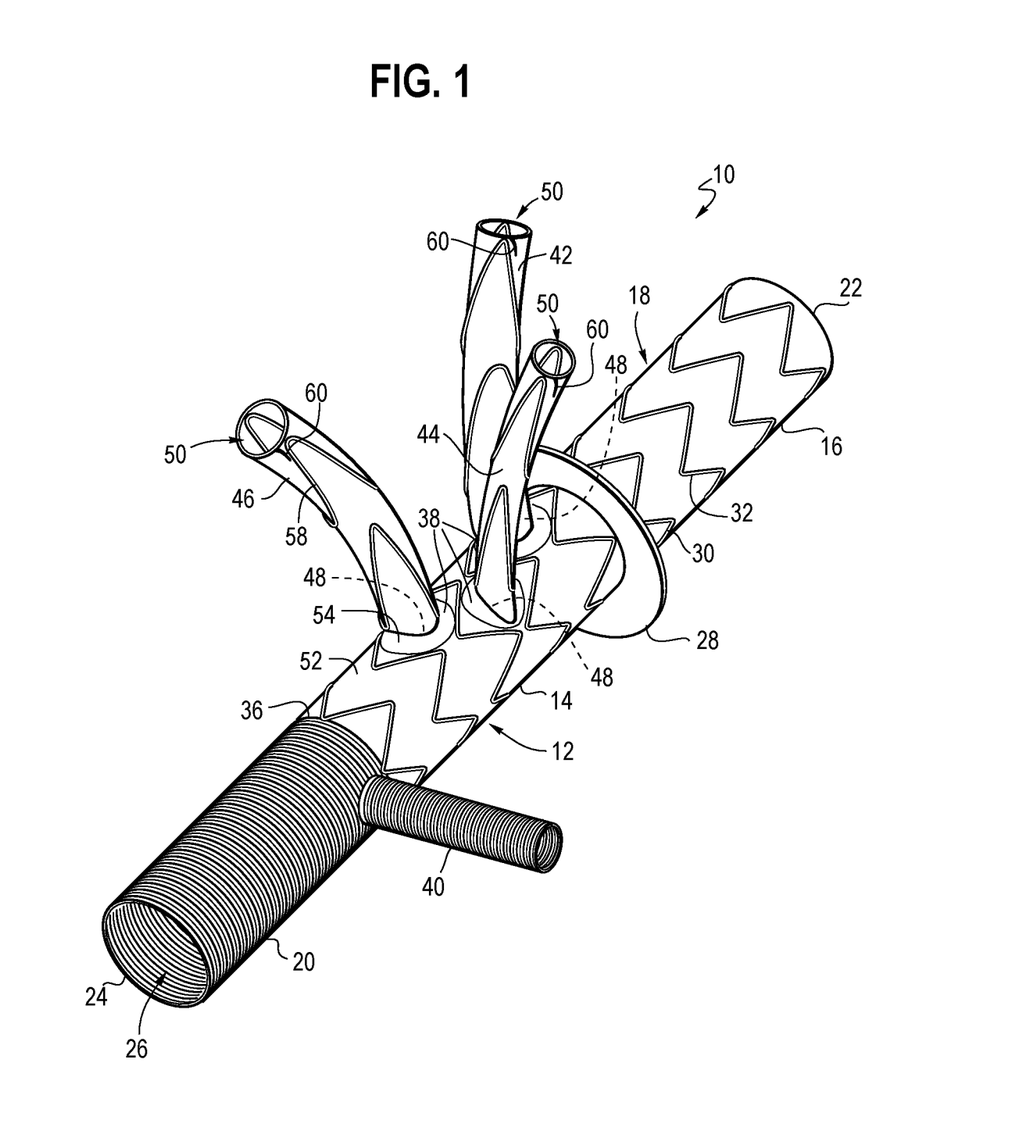
FIG. 1 shows a prosthesis for an aortic arch, according to a first aspect of the present invention.
Figure 2A:
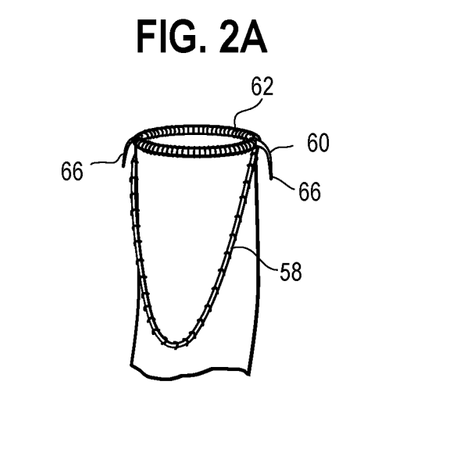
FIGS. 2A and 2B show detail views of the prosthesis of FIG. 1.
Figure 2B:
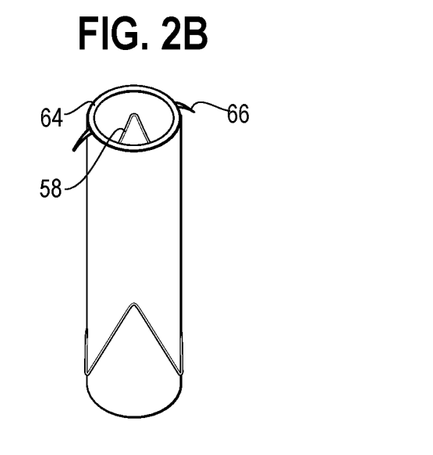
Figure 3A:
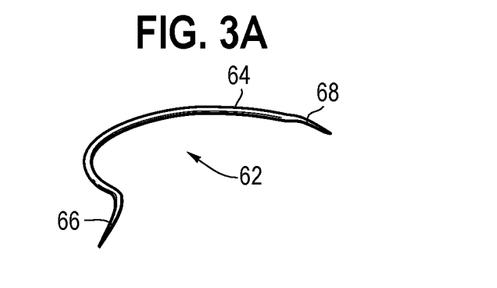
FIGS. 3A and 3B show wire segments as used in the prosthesis of FIG. 1.
Figure 3B:
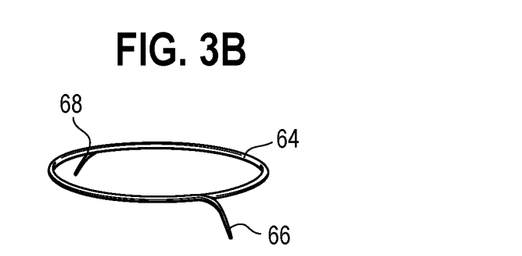

FIGS. 1-3 illustrate one example of a prosthesis 10. The prosthesis 10 includes a graft 12 having a tubular main body 14. The main body 14 includes a distal portion 16, a middle portion 18, and a proximal portion 20.

The distal portion 16 includes a distal end 22 defining a distal opening. The proximal portion 20 includes a proximal end 24 defining a proximal opening. The middle portion 18 extends between the distal portion 16 and the proximal portion 20.

As shown in FIG. 2, the graft 12 is configured as a tubular member having a substantially cylindrical shape, and includes an inner surface and an outer surface. The inner surface thereby defines a lumen 26 extending from the proximal end 24 to the distal end 22. The lumen 26 extending longitudinally through the graft 12, and is configured to allow fluid to pass therethrough from the proximal end 24 to the distal end 22, such as blood.

The graft 12 may further include a collar 28 disposed at the intersection between the distal portion 16 and the middle portion 18. The collar 28 is configured for being sutured to the descending aorta to create an anastomosis between the graft 12 and the descending aorta. The collar 28 may project radially from the outer surface of the graft 12, having the shape of an annular flange. The collar 28 may have a fixed shape to project radially outward from the graft 12. Alternatively, the collar 28 may be formed from excess graft material that projects radially outward in response to relative longitudinal compression of the distal portion 16 toward the middle portion 18, such that this compression will cause the graft material to be pushed outward to define the collar 28.

The graft 12 may further include at least one support structure 30, such as a stent. The support structure 30 may be in the form of a single, unitary, monolithic structure, or it may be in the form of multiple individual structures. In one form, the support structure 30 is a plurality of Z-stents 32 that may be radially compressed into a delivery configuration, where the stents are biased radially outward, and will expand radially outward in response to removing a radial retention mechanism, such as a sheath or diameter reducing ties 34.

The support structure 30 may be disposed along the distal portion 16 along substantially the entire length of the distal portion 16. The support structure 30 may also be disposed along the middle portion 18 along substantially the entire length of the middle portion 18, except for distinct areas of the middle portion 18 where additional structure is provided.

The proximal portion 20 may be free from any additional support structure such as stents. The middle portion 18 may transition to the proximal portion 20 at a junction 36. The middle portion 18 may be made from a different graft material than the proximal portion 20, with the junction 36 being defined by the transition between different graft materials. In one form, the proximal portion 20 may be a Dacron graft material.

The middle portion 18 may include a plurality of passageways 38 disposed through the graft material of the main body 14 to permit fluid to pass therethrough from the lumen 26 to an area outside of the main body 14. The passageways may also be referred to as fenestrations.

In one example, there are three passageways 38 disposed in the middle portion 18. The passageways 38 may be arranged adjacent each other and on the same circumferential side of the graft 12. These three passageways 38 may be used to communicate with the innominate, left common carotid and left subclavian arteries (the branch vessels).

The proximal portion 20 may further include a perfusion side branch 40. The perfusion side branch 40 may be used for antegrade perfusion during repair of the ascending aorta. The perfusion side branch 40 extends radially outward from the proximal portion 20 and provides fluid communication to the lumen 26.

The passageways 38 may be connected to connection branches 42, 44, and 46 or may be a part of the connection branches 42, 44, and 46. In the shown embodiment, the prosthesis 10 includes three connection branches 42, 44, and 46 disposed respectively at each of the passageways 38. The connection branches 42, 44, and 46 each define an inner opening 48 at an inner end and an outer opening 50 at an outer end with a lumen 26 extending between the inner opening 48 and the outer opening 50. The connection branches 42, 44, and 46 provide fluid communication from the inner opening 48 to the outer opening 50 via the lumen 26. The connection branches 42, 44, and 46 are disposed at the passageways 38, such that the inner opening 48 may be disposed at the passageway 38 that provides fluid communication through the wall 52 of the main body 14.

In one form, the passageways 38 include a support structure 54 attached to the main body 14 of the graft 12. The support structure 54 may be used to keep the passageway 38 open, and may also be used to attach the connection branch to the body of the graft 12. One or more of the connection branches 42, 44, and 46 may be attached to the middle portion 18 of the graft 12 such that the connection branches 42, 44, and 46 are disposed externally outside the lumen 26 of the graft 12. In this approach, the inner end at the inner opening 48 of the respective connection branch 42, 44, or 46 may correspond to the location of the support structure 54 of the passageway 38, with the outer opening 50 forming an outer end disposed radially away from the body of the graft 12. In this approach, fluid in the lumen 26 may enter the connection branch 42, 44, or 46 at the location of the support structure 54 in the sidewall of the graft 12, and may pass through the outer end at a location radially away from the sidewall of the graft 12 and the support structure 54.

The connection branches 42, 44, and 46 include a support structure 56 to maintain patency for allowing fluid to flow therethrough. The support structure 56 may include traditional Z-stents or spiral Z-stents. The connection branches 42, 44, and 46 may also include a seal stent 58 disposed near the outer end of the connection branch, schematically shown in FIGS. 2A and 2B. The seal stent 58 is preferably disposed on the inner surface of the tubular connection branch, thereby leaving the outer surface of the connection branch 42, 44, or 46 generally smooth as indicated in FIG. 2B. The seal stent 58 may improve sealing of the connection branch 42, 44, or 46 to the branch vessel when deployed.

The outer end of at least one of the connection branches 42, 44, and 46 further includes an anchoring structure 60 for retaining the connection branches 42, 44, and 46 in their respective branch vessel. The anchoring structure 60 is composed of at least two wire segments 62 as shown in FIGS. 3A and 3B. Each wire segment 62 has an arc portion 64 forming a partial ring, and a barb portion 66. The arc portion 64 of each wire segment 62 extends over an angular distance that depends on the number of wire segments 62 used. For example, if, as shown in FIG. 3B, two wire segments 62 are used, the arc portion 64 extends over about half a circle, i.e. 180°±5°. If more wire segments 62 are used, each arc portion 64 extends over about 360° divided by the number of wire segments 62 within a variance of ±5°.

The barb portion 66 is disposed at one circumferential end of the arc portion 64. The barb portion 66 of one wire segment 62 is adjacent to a barb-free end 68 of the arc portion 64 of an adjacent wire segment 62. The barb portion 66 is deflected from the arc portion 64 in a radially outward direction and in an axial direction toward the inner end at the inner opening 48 of the respective connection branch. The barb portion 66 has a length that is smaller than the diameter of the connection branch, for example about 10% or 20% of the diameter.

Preferably, the number of wire segments 62 is an even number to facilitate a collapse of the anchoring structure 60 by folding the wire segments toward each other about at least one pivot axis X. The number of pivot axes corresponds is half the number of wire segments, i.e. one pivot axis X for two wire segments, two preferably perpendicular pivot axes for four wire segments, three pivot axes rotated by 60 degrees relative to one another for six wire segments, etc. While two wire segments 62 as shown in FIG. 3B may enhance the stability of the anchoring structure 60 by spanning the entire diameter of the connection branch 42, 44, or 46 and by protecting the wire segment 62 against tilting after expansion. This supports a proper piercing of the surrounding body vessel wall by the barb portion 66. The use of a seal stent 58, however, may allow for the use of four wire segments 62 that each cover a only about a quarter circle because the seal stent 58 provides sufficient radial stability.

Figure 4:
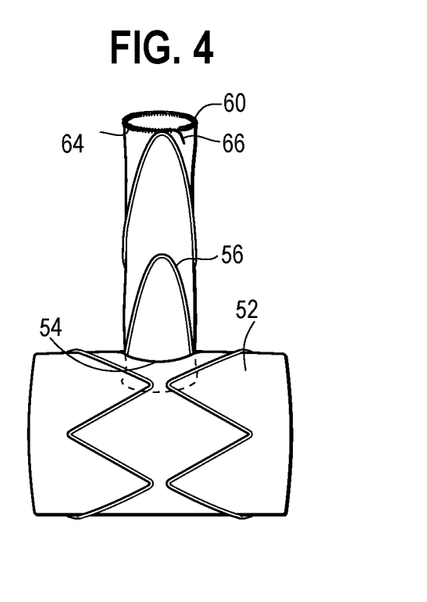
FIG. 4 shows a detail of the prosthesis of FIG. 1 with an expanded connection branch.

FIG. 4 shows a partial prototype of the endoluminal device with one connection branch 42 shown as an example that may represent any of the connection branches 42, 44, and 44 shown in FIG. 1. FIG. 4 shows the connection branch 42 in its expanded state that is assumed after delivery.

For collapsing the connection branch 42, the two wire segments 62 of FIG. 3B are folded toward the inner end of the connection branch about a pivot axis X extending through the two locations where the two arc portions 64 meet. Where four wire segments 62 are used, they can be folded into a zigzag structure.

Figure 5A:
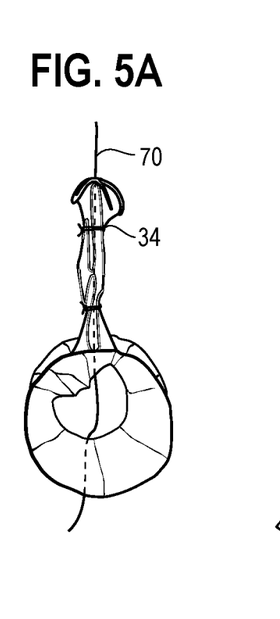
FIGS. 5A and 5B show details of the prosthesis of FIG. 1 with a compressed connection branch.
Figure 5B:
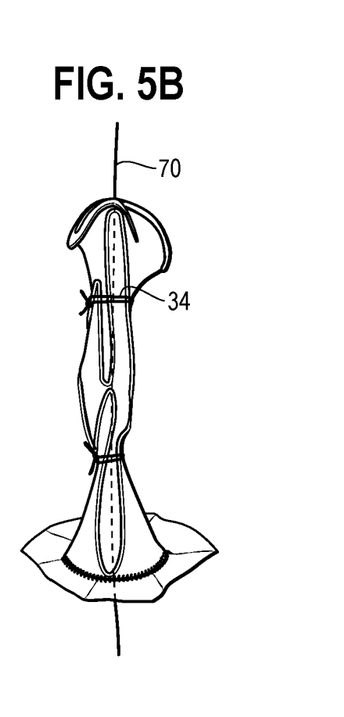

In one approach and schematically shown on the prototype in FIGS. 5A and 5B, the remaining length of the connection branches 42, 44, and 46 may be retained in a compressed delivery configuration using diameter reducing ties 34. The diameter reducing ties 34 are held together via trigger wires 70, and keep the connection branch compressed radially. Retracting the trigger wires 70 will release the ties 34 from each other, allowing the connection branch 42 to expand radially outward. The resilient force of the support structure 54 of the connection branch 42 expands the graft material and unfolds the wire segments 62 to form a circle at the outer end adjacent the ring-shaped anchoring structure 60 formed by the wire segments 62.

The connection branches 42, 44, and 46 may be preferably arranged to allow the connection branches 42, 44, and 46 to pivot relative to the graft 12 for obtaining a reduced cross-section of the graft 12 during delivery.

The inner end of one or more of the connection branches 42, 44, and 46 may be sewn onto a fenestration in the body of the graft 12, where the fenestration defines the passageway 38.

The connection branches 42, 44, and 46 are sized and arranged such that they will extend into the branch vessels by a sufficient length where the seal stent 58 and/or the anchoring structure 60 will reach a landing zone within the branch vessel of interest. Thus, the connection branches 42, 44, and 46 will have a length sufficient to extend into the branch vessels, and fluid flowing from the lumen 26 of the graft 12 will flow through the connection branches 42, 44, and 46 and exit the connection branches 42, 44, and 46 within the respective branch vessels. The connection branches 42, 44, and 46 therefore preferably do not mate with additional branch extensions or the like.

The connection branches 42, 44, and 46 have a pre-defined length. This pre-defined length is known to the surgeon, and therefore allows the surgeon to easily determine the length that the connection branch 42, 44, or 46 has been deployed into the branch vessel. For example, the amount or length that the connection branch 42, 44, or 46 has been extended into the vessel can be determined by taking the overall pre-defined length of the connection branch 42, 44, or 46 and subtracting the remaining length of the connection branch 42, 44, or 46 that remains outside of the branch vessel. This is easily determined by observing or measuring the length of the connection branch 42, 44, or 46 that remains outside of the branch vessel. Accordingly, the physician can quickly and easily determine whether the connection branch 42, 44, or 46 has been inserted a sufficient/desired amount into the branch vessel such that the surgeon can know with increased confidence that the connection branch 42, 44, or 46 has been inserted to allow for sustained blood flow into the branch vessel.

In an alternative embodiment shown in FIGS. 6A, 6B, 7A, and 7B, the prosthetic device may be a modular assembly, in which the main body and the connection branches 42, 44, and 46 are individually and separately selected based on the underlying anatomy of the respective patient. In this manner, lengths or diameters or both can be instantly matched with the patient.

Figures 6A, 6B, 7B:
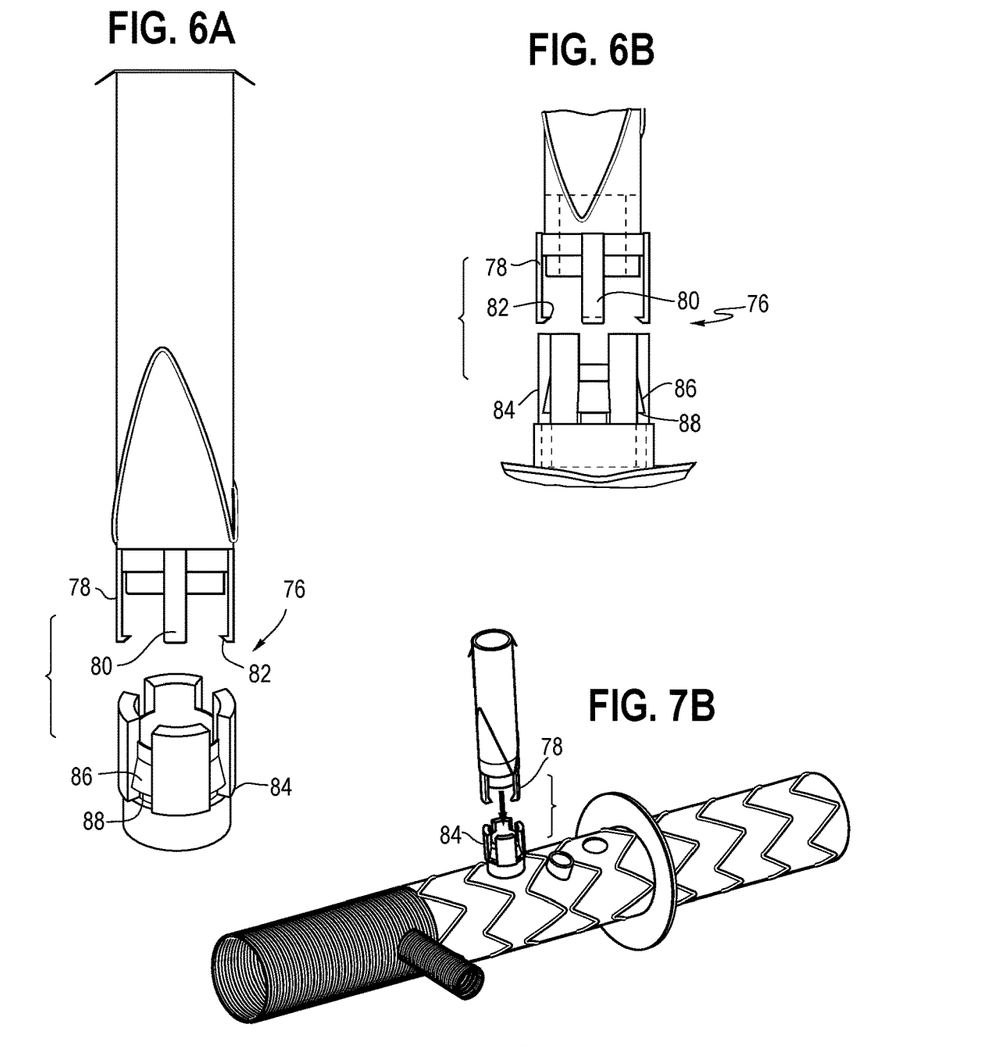
Figure 7B:
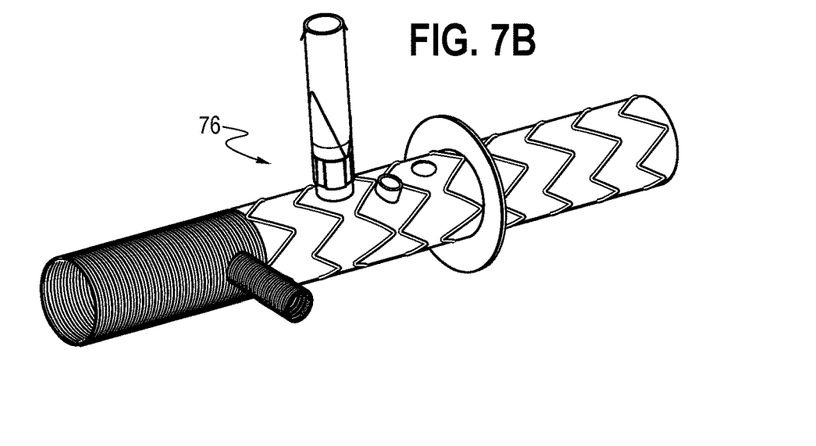

FIGS. 6A and 6B show an example of a snap-fit quick connector 76 that allows a form-fitting connection between the connection branch 42, 44, or 46 and the main body with a single movement. In the shown example, the inner end of the connection branch 42, 44, or 46 has a first connector part 78 with a central passageway 38 and with a plurality of snap fingers 80 distributed about the circumference of the first connector part 78. The snap fingers 80 have free ends with inward projections 82 dimensioned to latch into an indentation on a second connector part 84 affixed to the main body of the graft. The second connector part 84 has a number of tapers 86 equal to the number of snap fingers 80 on the first connector part 78. In the longitudinal direction of the connection branch, each taper 86 forms a radially outward slope toward an inward step 88 that delimits the indentation receiving the inward projections 82. The inward steps 88 are dimensioned to cooperate with the inward projections of the snap fingers to form a positive lock once the projections snap into place after passing the inward step 88. Between the tapers 86, the second connector part 84 has axial walls forming a smooth surface with the outer surfaces of the snap fingers 80 so that the quick connector 76 has a smooth cylindrical outer surface upon assembly of the first connector part 78 and the second connector part 84. The connection between the first connector part 78 and the second connector part 84 is releasable and reconnectable, e.g. to attach a differently sized connection branch, by expanding the snap fingers 80 radially outward with a suitable tool. Thus, the prosthesis 10 remains customizable up to the point of implantation.

Without limitation, the second connector part 84 may be attached to the main body 14 via a swivel connection by providing sufficient surrounding graft material to align the connection branches with the longitudinal direction of the main body. The quick connector 76 is preferably formed from a resilient plastic material.

It should be noted that the quick connector 76 of FIGS. 6A through 7B is only one example for assembling a modular prosthesis. For example, a ratchet connection, a threaded connection, or a press fit connection are all feasible options For a ratchet connection, for example, each of the snap arms may have a plurality of successive projections 82 or teeth, and the second connector part 84 may have a plurality of successive tapers 86 and steps for each of the snap arms. The physical forces acting on the connector after implantation are limited. The connection branches 42, 44, and 46 are sufficiently stabilized via the seal stent 58 or the barbs or both so that a thermoplastic connector provides a sufficient strength.

Depending on the force required to connect the first and second connector parts 78 and 84, the complete prosthesis may be assembled prior to delivery or in situ. The following description of the delivery process assumes assembly prior to delivery. While the illustrations show the prosthesis 10 of FIGS. 1-5, the delivery process is applicable to the embodiment of FIGS. 6 and 7 in analogy.

The connection branches 42, 44, and 46 are arranged to be inserted into the branch vessels using the endovascular technique of delivering a radially compressed body over a wire. Accordingly, the connection branches 42, 44, and 46 have a compressed delivery state and an expanded deployed state.

The connection branches 42, 44, and 46 may be delivered in a compressed state over a wire into the branch vessels. The compressed delivery state allows the connection branches 42, 44, and 46 to easily navigate the interior of the branch vessel such that they will reach the desired landing zone. As described above, the surgeon can easily determine by direct observation the amount that the branch is extended into the branch vessel by observing the amount of the branch that is exposed, allowing the surgeon to reposition the branch as needed prior to expanding the connection branch.

To deliver the connection branches 42, 44, and 46 into engagement with the corresponding branch vessel, a plurality of wires 74 may be provided. The wires may also be referred to as SAT wires ("supra aortic trunk" wires). The wires may delivered into the patient's body through micropuncture of the right and left brachial arteries and left common carotid arteries, and may be guided via ultrasound. The wires may be delivered into the arch supra aortic trunk, and out of the branch vessels.

With the wires extending out of the branch vessels, the outer ends of the connection branches 42, 44, and 46 may be inserted over the wires, with the wires guiding the connection branches 42, 44, and 46 into the corresponding branch vessels.

In another approach, as schematically shown in FIGS. 5A and 5B, the wires may be pre-loaded within the prosthesis 10. In this approach, the wires will not be delivered via micropuncture, but will be delivered out of the prosthesis 10 and into the branch vessels prior to advancing the connection branches 42, 44, and 46 into the branch vessels. In the pre-loaded state, the wires extend through the proximal end 24 of the graft 12 and into the lumens of the connection branches 42, 44, and 46. In the delivery state of the prosthesis 10, the wires preferably terminate before the outer end of the connection branch. The end of the SAT wire is shown in FIGS. 5A and 5B only for illustration and would preferably not protrude on an actual prosthesis 10.

To deliver the connection branches 42, 44, and 46 into the branch vessels, the wires are advanced out of the outer ends of the connection branches 42, 44, and 46 and into the corresponding branch vessels. With the wires extending into the corresponding branch vessels, the connection branches 42, 44, and 46 may be delivered in their compressed delivery state over the connection branches 42, 44, and 46. With the connection branches 42, 44, and 46 in their desired location, the braches may be expanded radially into engagement with the branch vessels.

Figure 8:
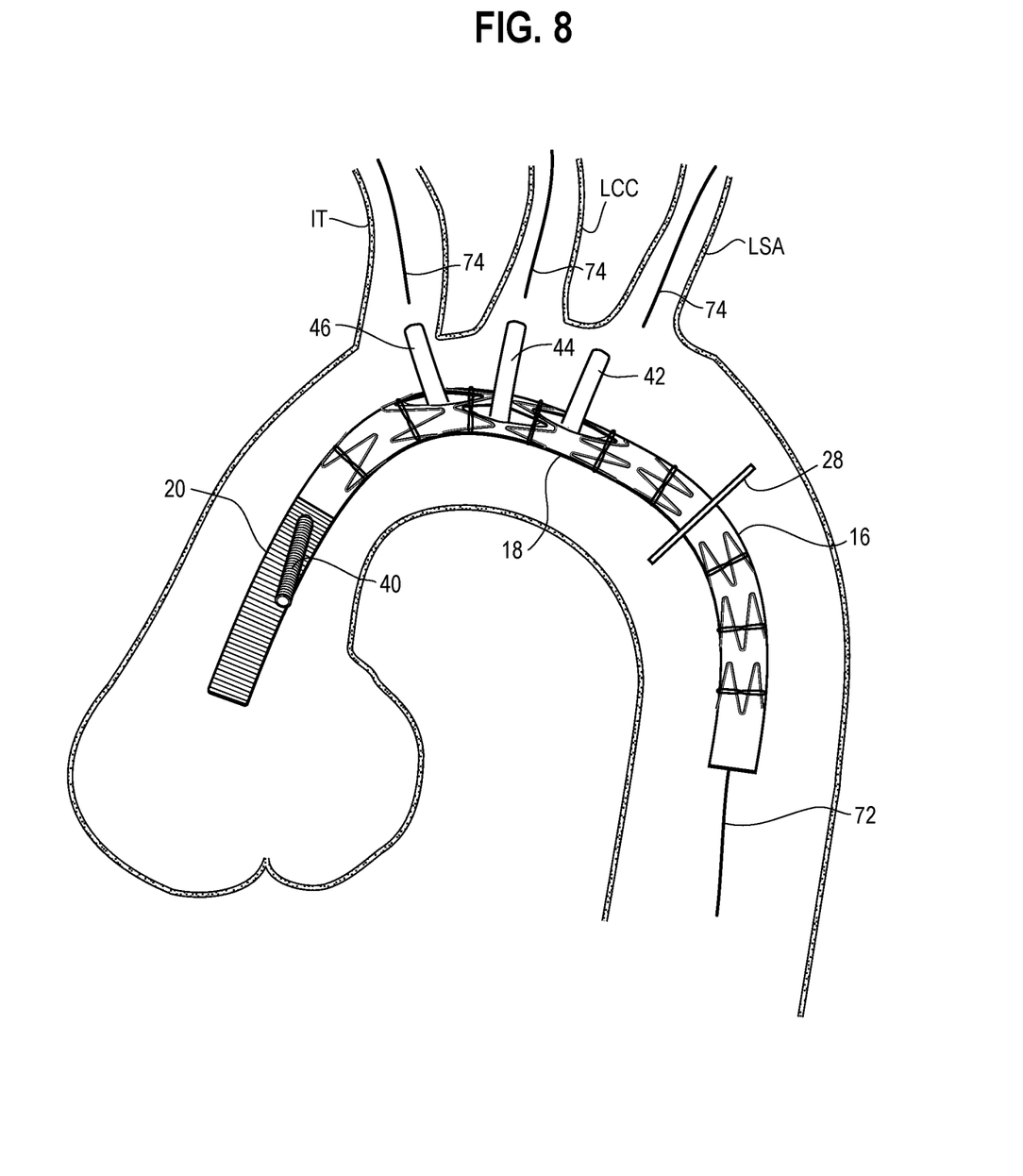
FIGS. 8, 9, 10, and 11 show different stages of implantation of a prosthesis for an aortic arc by the example of the embodiment of FIG. 1.

For example, FIG. 8 shows the prosthesis in a compressed delivery configuration. The distal portion 16 of the graft 12 may have a compressed delivery configuration established by a restraining sheath that surrounds and compresses the distal portion 16 therein. The restraining sheath may be a peel away sheath or a push/pull sheath. In another approach, the distal portion 16 may be compressed radially via the use of diameter reducing ties 34. Diameter reducing ties 34 were described above and utilizes a trigger wire 70 to release the ties 34 and allow the stents to expand. Retracting the trigger wires 70 allows the loops of the ties 34 to separate from each other, and the graft 12 may expand.

The middle portion 18 can likewise be compressed radially through the use of the diameter reducing ties 34. With the middle portion 18 of the main body 14 compressed, the ostiums of the branch vessels may be more easily visualized and accessed.

The above-described prosthesis may be delivered as follows. With reference to FIG. 8, a femoral wire 72 may be introduced into the descending aorta via femoral puncture in a traditional manner. The femoral wire 72 will be inserted into the patient's body through femoral puncture and routed into the descending aorta to a location near the branch vessels and a desired location for the distal portion 16 of the prosthesis 10.

The SAT wires 74 may be introduced via micropuncture of the left and right brachial arteries and left common ceratoid artery. The wires may be guided by ultrasound and routed to the arch supra aortic trunk, such that the wires will extend out of the branch vessels, in particular the innominate trunk (IT), the left common carotid (LCC) artery, and the left subclavian artery (LSA). With the ends of the wires and disposed within the aortic arch, the wires and are accessible to the surgeon for further use with the prosthesis 10.

The surgeon may institute cerebral perfusion through the right axillary and left common carotid arteries.

The prosthesis 10 may then be delivered into the descending aorta. In particular, the prosthesis 10 may be part of a delivery system where the distal portion 16 and middle portion 18 are in a radially compressed state. The compressed distal portion 16 may be inserted into the descending aorta over the femoral wire 72. The connection branches 42, 44, and 46 are disposed within their sheaths or compressed via the diameter reducing ties 34. FIG. 8 illustrates branches compressed and does not illustrate the ties 34 for clarity, but the diameter reducing ties 34 would also apply to FIG. 8. FIG. 8 illustrates diameter reducing ties 34 for compression of the distal portion 16, but the sheath could also be used for FIG. 8.

Figure 9:
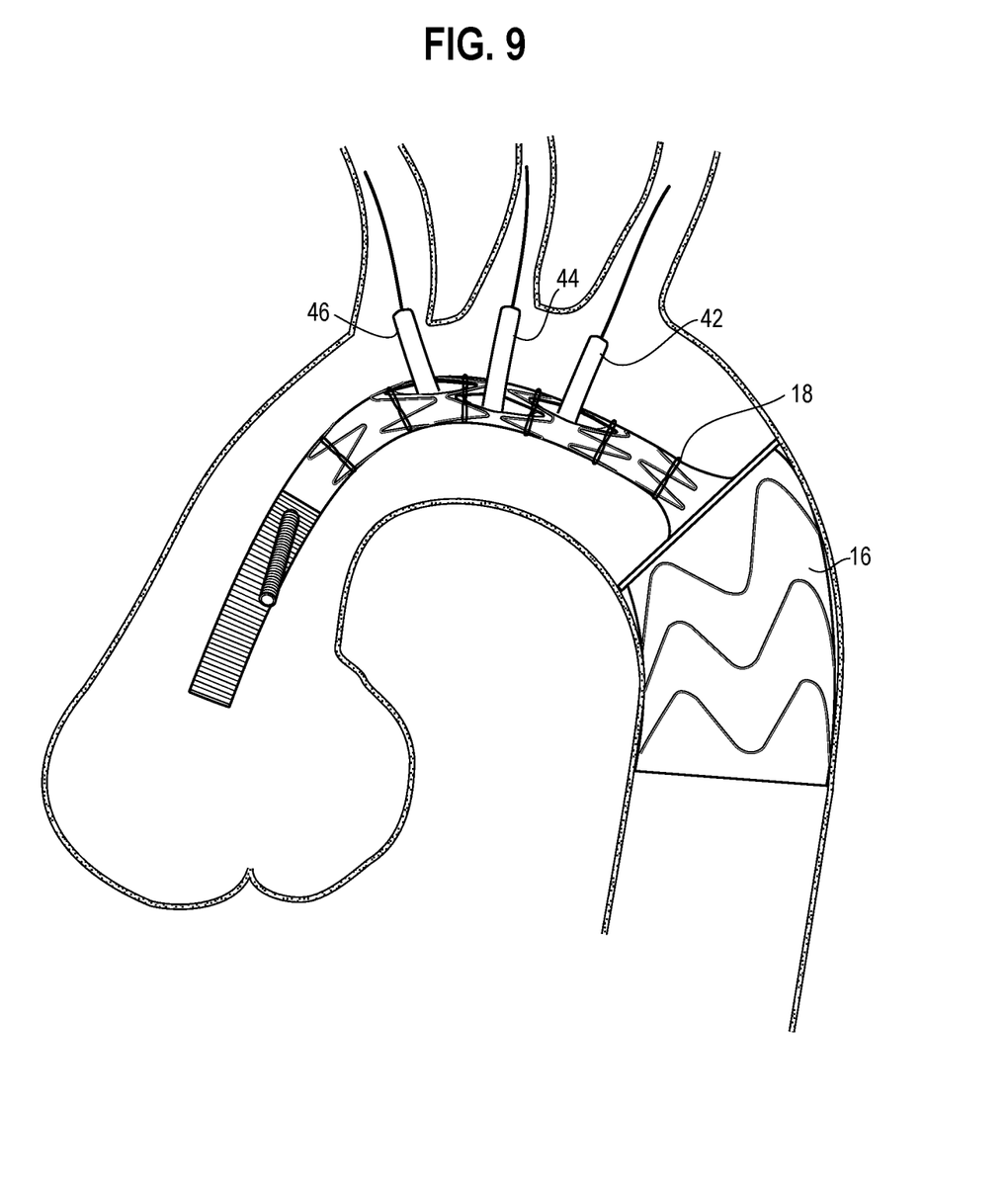

As shown in FIG. 9, with the distal portion 16 in the desired location, the distal portion 16 may be allowed to expand into engagement with the vessel wall. In the case of a peel-away sheath, the sheath may be peeled-away, exposing the distal portion 16 and allowing the support structure 54 to cause the distal portion 16 to expand. In the case of a push-pull sheath, the sheath may be advanced distally to expose the distal portion 16 and allow it to expand, and then retracted back through the prosthesis 10 after the distal portion 16 has expanded. In the case of diameter reducing ties 34, the ties 34 may be released, allowing the distal portion 16 to expand.

After the distal portion 16 has expanded, the collar 28 may be sutured to the aortic wall to create an anastomosis. At this point, the prosthesis 10 is "frozen" at the distal portion 16 and the collar 28, such that the prosthesis 10 will stay in place. The anastomosis created by suturing the collar 28 blocks flow that may occur outside of the prosthesis 10 once deployed.

With access to the SAT wires 74, the wires may be loaded into the connection branches 42, 44, and 46, such that the wires will enter the outer end of each of the connection branches 42, 44, and 46. The wires provide a routing function for the connection branches 42, 44, and 46.

Figure 10:
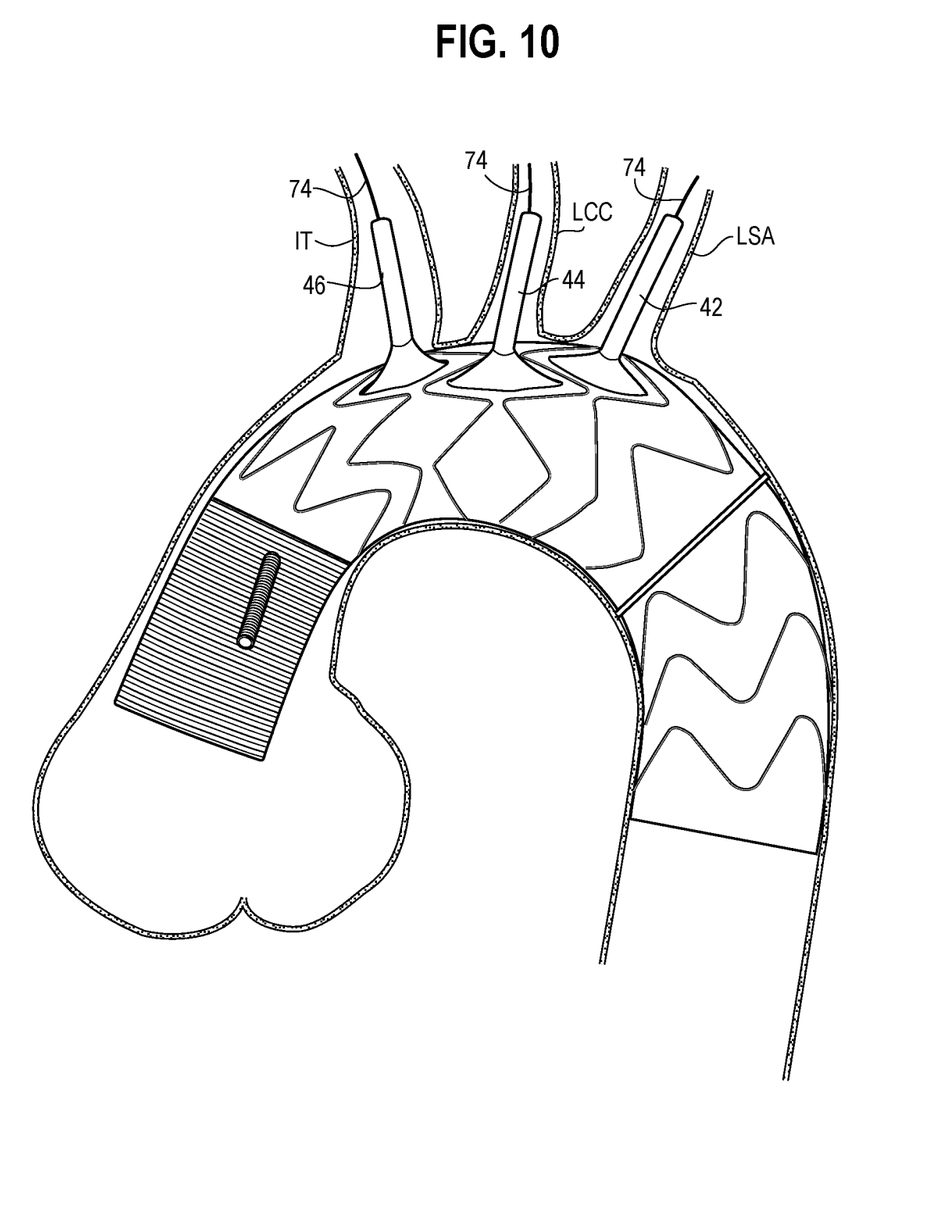

With reference to FIG. 10, the middle portion 18 of the prosthesis 10 may be released from its radially compressed delivery state by releasing the diameter reducing ties 34. The middle portion 18 will expand radially into engagement with the vessel wall. Unlike the distal portion 16, suturing or creating an anastomosis for the middle portion 18 may not be performed.

As further shown in FIG. 10, with the middle portion 18 expanded, the connection branches 42, 44, and 46 may then be advanced over the wires into the corresponding branch vessels. The connection branch 42 for the LSA may be advanced first. The connection branch 42 has a compressed delivery state, and may be advanced over the wire SAT wire 74 placed in the LSA. Once the connection branch 42 is in its desired location, the connection branch 44 may be released by releasing the diameter reducing ties 34. The LSA connection branch 42 at this point is deployed and held in place by its radially outward engagement with the vessel wall. The perfusion cannula (not shown) used for cerebral perfusion may be retracted out of the LCC for delivery of the corresponding connection branch 44 thereto. After retrieving the perfusion cannula, the connection branch 44 for the LCC will be delivered over the wire and into the branch vessel. The connection branch 44 will then be expanded from its delivery state to its deployed state in the manner described above. With the connection branch 44 deployed within the LCC, the perfusion cannula will be repositioned into the connection branch 44 of the LCC. Next, the connection branch 46 for the IT will be delivered over the wire and into the IT. The connection branch 46 will be released and expanded as described above. At this point, each of the branch vessels have received their corresponding connection branch 42, 44, or 46, respectively, and fluid communication from the interior of the prosthesis 10 to the branch vessels is possible.

FIG. 10 illustrates all of the connection branches 42, 44, and 46 being deployed within the corresponding branch vessels.

The proximal portion 20 of the prosthesis is subsequently deployed. More particularly, the proximal portion 20, which may be a wrapped Dacron material, may be unwrapped. The proximal portion 20 may then be flushed. The perfusion cannula extending into the LCC graft extension may be retrieved, and the proximal portion 20 may be clamped.

The perfusion side branch 40 extending from the proximal portion 20 may then be flushed, and the perfusion cannula is inserted into the side branch 40. Antegrade perfusion may then be started through the side branch 40, with the perfusion passing through the interior of the prosthesis 10.

The proximal portion 20 may then be sutured to the ascending aorta and the proximal ascending repair may be completed. The proximal portion 20 may be unclamped, the perfusion cannula may be removed from the side branch 40 and closed in a traditional manner, and the patient may be taken off bypass in a traditional manner.

This method allows for a reduction in the number of suturing steps and anastomoses that are created during the aortic repair. The delivery of elongated connection branches 42, 44, and 46 over the SAT wires 74 rather than creating anastomoses greatly reduces the amount of time in the procedure, increasing the likelihood of successful repair and reducing the time spent on bypass. Moreover, the use of the connection branches 42, 44, and 46 that completely extend from the body of the graft 12 into the branch vessels reduces the amount of connections that are made between components, increases the ability to determine the length of insertion, and reduces deployment forces on the graft 12.

Figure 11:
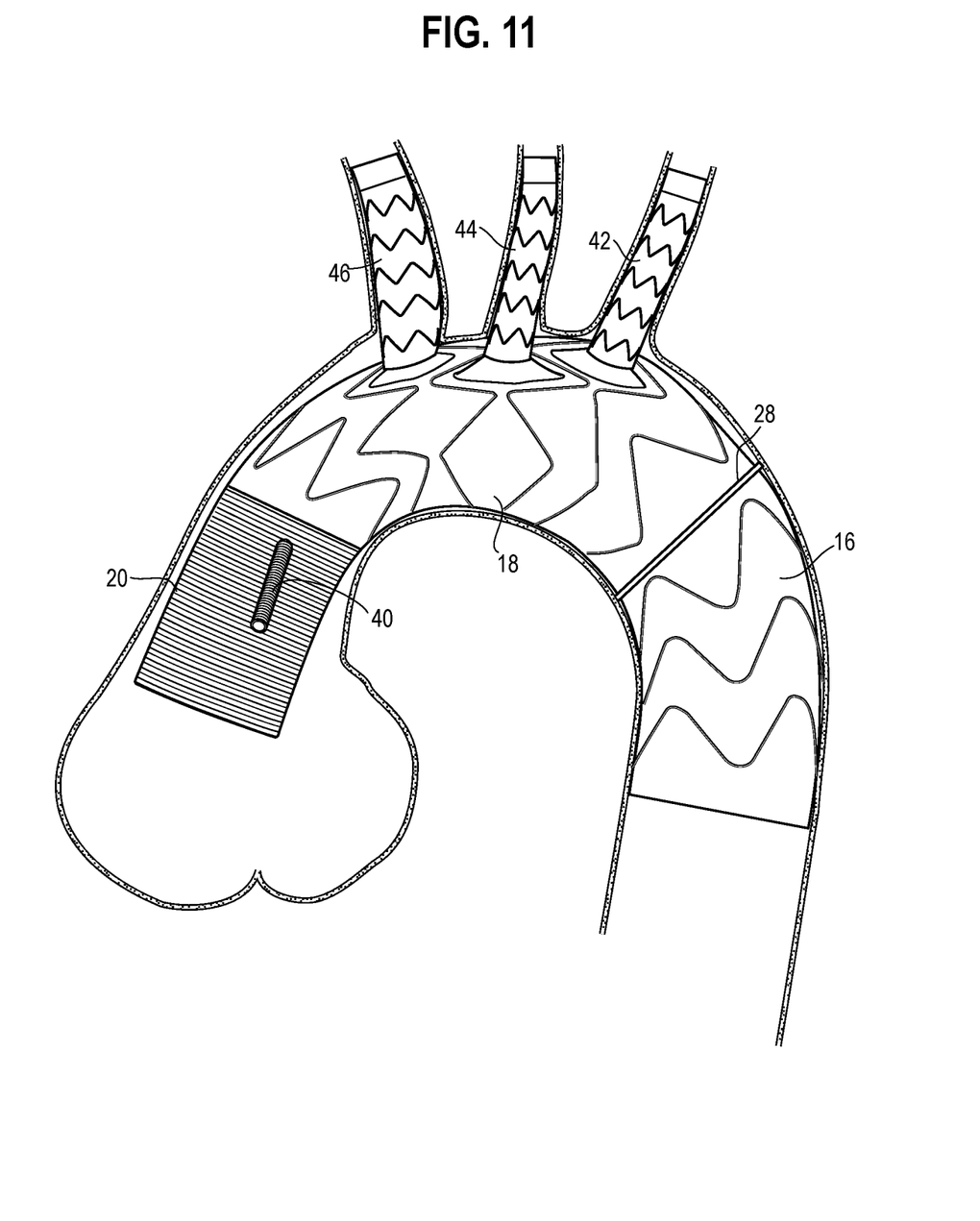

The above method may also be performed using the preloaded wires rather than SAT wires 74. In this approach, the wires are not routed through the patient's body and out of the branch vessels. Rather, after creating the distal anastomosis and expanding the middle portion 18 of the prosthesis, the preloaded wires may be extended out of the ends of the connection branches 42, 44, and 46 and into the corresponding branch vessels. The order in which the wires may be delivered into the branch vessels may vary. After the wires are extended out of the connection branches 42, 44, and 46 after the middle portion 18 is expanded, the implanted prosthesis has a configuration like the one shown in FIG. 11.

The connection branches 42, 44, and 46 may be delivered over the preloaded wires and deployed in the same manner as described above, and proximal repair may be performed similarly after deploying the connection branches 42, 44, and 46. Preferably, the connection branches 42, 44, and 46 are delivered to the branch vessels in the order of LSA, LCC, and IT, as described above.

In another approach, the preloaded wires may be extended out of the connection branches 42, 44, and 46 prior to expanding the middle portion 18, and the middle portion 18 may be expanded after extending the wires into the branch vessels. Preferably, the middle portion 18 is expanded prior to delivering the connection branches 42, 44, and 46 over the wires, because after the connection branches 42, 44, and 46 are deployed, radial expansion of the middle portion 18 would exert a radially outward force on the connection branches 42, 44, and 46 that have anchored in the branch vessels. In this approach, the illustration of FIG. 9 would apply after the wires are extended out of the connection branches 42, 44, and 46, but before expanding the middle portion 18.

Throughout this specification various indications have been given as to preferred and alternative examples and aspects of the invention. However, the foregoing detailed description is to be regarded as illustrative rather than limiting and the invention is not limited to any one of the provided aspects.

The invention claimed is:

1. An endoluminal prosthesis system for being deployed in a patient's aorta near the heart, the system comprising:
   a graft having a main body with a proximal end and a distal end, where the proximal end is an end configured to be deployed near a patient's heart and the distal end is an end configured to be deployed away from the patient's heart, the main body defining a lumen extending from the proximal end to the distal end;
   a proximal portion of the graft including the proximal end;
   a distal portion of the graft including the distal end;
   a middle portion of the graft extending between the proximal portion and the distal portion;
   at least one connection branch attached to the middle portion, the connection branch having an inner end attached to the middle portion and an outer end disposed radially outwardly from the inner end, and a lumen extending from the inner end to the outer end, wherein the at least one connection branch provides fluid communication from the lumen of the graft, through the lumen of the connection branch to the outer end;
   wherein the outer end of the at least one connection branch is defined by a terminal ring composed of at least two partial rings pivotable relative to each other, each of the at least two partial rings including at least one radially outward barb; and
   wherein the connection at least one branch has a compressed delivery configuration, in which the partial rings are folded toward one another, and an expanded deployed configuration, in which the partial rings form a full ring.

2. The system of claim 1, wherein the partial rings are pivotable relative to each other about an axis perpendicular to a longitudinal direction of the lumen of the connection branch.

3. The system of claim 1, wherein the at least one connection branch includes a seal stent disposed adjacent the outer end, the seal stent being biased radially outward to engage a branch vessel wall.

4. The system of claim 3, wherein the at least one connection branch are stented such that additional stents are disposed inwardly relative to the seal stent.

5. The system of claim 1, wherein each partial ring is monolithically formed with the at least one barb.

6. The system of claim 1, wherein the terminal ring consists of an even number of partial ring.

7. The system of claim 1, wherein the inner ends of the connection branch attached to the middle portion at an attachment portion, wherein the attachment portion includes a flexible portion of graft material, and the inner end of the connection branch is sewn to the flexible portion of graft material.

8. The system of claim 1, wherein the proximal portion is unstented and includes a perfusion side branch extending radially outward from the proximal portion.

9. The system of claim 1 further comprising at least one wire configured to extend through the at least one connection branch and out of the distal end of the graft in the delivery configuration.

10. The system of claim 1 further comprising an annular collar disposed at an intersection between the distal portion and the middle portion.

11. An endoluminal prosthesis system for being deployed in a patient's aorta near the heart, the system comprising:
   a graft having a main body with a proximal end and a distal end, where the proximal end is an end configured to be deployed near a patient's heart and the distal end is an end configured to be deployed away from the patient's heart, the main body defining a lumen extending from the proximal end to the distal end;
   a proximal portion of the graft including the proximal end;
   a distal portion of the graft including the distal end;
   a middle portion of the graft extending between the proximal portion and the distal portion;
   at least one connection branch attached to the middle portion via a releasable quick connector, the connection branch having an inner end attached to the middle portion and an outer end disposed radially outwardly from the inner end, and a lumen extending from the inner end to the outer end, wherein the at least one connection branch provides fluid communication from the lumen of the graft, through the lumen of the connection branch to the outer end;
   wherein the outer end of the at least one connection branch is defined by a terminal ring composed of an even number of partial rings pivotable relative to each other, each of the partial rings including at least one radially outward barb; and
   wherein the connection at least one branch has a compressed delivery configuration, in which the partial rings are folded toward one another, and an expanded deployed configuration, in which the partial rings form a full ring.

* * * * *